United States Patent [19]

Kilbourn et al.

[11] Patent Number: 5,334,380

[45] Date of Patent: Aug. 2, 1994

[54] ANTI-ENDOTOXIN, INTERLEUKIN-1 RECEPTOR ANTAGONIST AND ANTI-TUMOR NECROSIS FACTOR ANTIBODY WITH ARGININE-FREE FORMULATIONS FOR THE TREATMENT OF HYPOTENSION

[75] Inventors: Robert G. Kilbourn, Houston, Tex.; Owen W. Griffith, Milwaukee, Wis.; Steven S. Gross, New York, N.Y.

[73] Assignee: Board of Regents, The University of Texas System, Austin, Tex.

[21] Appl. No.: 910,868

[22] Filed: Jun. 30, 1992

Related U.S. Application Data

[63] Continuation-in-part of Ser. No. 767,265, Sep. 27, 1991, Pat. No. 5,286,739.

[51] Int. Cl.$^5$ ............... A61K 37/02; A61K 37/04; A61K 37/18
[52] U.S. Cl. ............... 424/85.2; 424/145.1; 424/150.1; 424/158.1; 424/164.1; 426/656; 514/12; 514/21
[58] Field of Search ............... 424/85.2, 85.8; 426/656; 514/12, 21

[56] References Cited

U.S. PATENT DOCUMENTS

| | | |
|---|---|---|
| 4,859,452 | 8/1989 | Ajani et al. . |
| 4,988,724 | 1/1991 | Ajani et al. . |
| 5,006,559 | 4/1991 | Askanazi et al. ............ 514/561 |
| 5,028,627 | 7/1991 | Kilbourn et al. . |
| 5,059,712 | 10/1991 | Griffith . |

FOREIGN PATENT DOCUMENTS

| | | |
|---|---|---|
| 0318446A1 | 5/1989 | European Pat. Off. ...... A61K 37/18 |
| WO91/84023 | 4/1991 | PCT Int'l Appl. ......... A61K 31/195 |
| PCT/US92/-08227 | 2/1993 | PCT Int'l Appl. . |

OTHER PUBLICATIONS

Moncada et al., "Nitric Oxide: Physiology, Pathophysiology, and Pharmacology," *Pharmacological Reviews*, 43(2):109–142, 1991, published in USA.
Moncada et al., "The L–Arginine: Nitric Oxide Pathway," *Journal of Cardiovascular Pharmacology*, 17 (Suppl. 3):S1–S9, 1991, published in USA.

(List continued on next page.)

*Primary Examiner*—Howard E. Schain
*Assistant Examiner*—Choon Koh
*Attorney, Agent, or Firm*—Arnold, White & Durkee

[57] ABSTRACT

Methods and compositions for treating and inhibiting hypotension related to both endotoxin and cytokine-induced shock are provided. A therapeutic regimen useful in the present invention includes an arginine-free parenteral formulation administered with or followed by the administration of an anti-endotoxin antibody, an interleukin-1 or interleukin-2 receptor antagonist, an anti-tumor necrosis factor antibody or a combination thereof. Most preferably, the administration of an arginine-free parenteral formulation augments the anti-hypotensive effect of the various antibodies and antagonist described so as to provide an effective treatment for various forms of hypotension. The therapeutic regimens of the invention are proposed to provide for a decrease in nitric oxide synthase, and thereby an increase in blood pressure in vivo, particularly in animals with cytokine- and/or endotoxin-induced hypotension. The parenteral formulation of the therapeutic regimen and methods of the invention are arginine-free and provide a decrease in plasma arginine levels. Reduced plasma, serum, or tissue levels of arginine in the animal function to augment the hypertensive action of the various antibodies and antagonist to be administered concurrently or subsequent to the administration of the parenteral formulation. Limiting and/or eliminating substrate arginine for nitric oxide synthesis, coupled with limiting and/or eliminating induction of nitric oxide synthase activity with the antibodies and antagonists of the present invention, provides a regimen for treating and/or inhibiting hypotension attendant a variety of conditions and treatments, including chemotherapeutic agent therapy (IFN, TNF, IL-1, IL-2), septic shock, trauma, exposure to endotoxins or cytokines, or other conditions in which hypotension is attendant.

23 Claims, 1 Drawing Sheet

OTHER PUBLICATIONS

Parratt, J. R., and Stoclet, Jean-Claude, "Possible Role of Nitric Oxide in Refractory Hypotension Associated with Sepsis and Endotoxaemia and with Multiple Organ Failure," *Applied Cardiopulmonary Pathophysiology*, 4:143–149, 1991, published in USA.

Johnston, Jeff, "Molecular Science Sets Its Sights On Septic Shock," *The Journal of NIH Research*, 3:61–65, 1991, published in USA.

Moncada, S., and Higgs, E. A., "Endogenous Nitric Oxide: Physiology, Pathology and Clinical Relevance," *European Journal of Clinical Investigation*, 21:361–374, 1991, published in Europe.

Martin et al., "Selective Blockade of Endothelium-Dependent and Glyceryl Trinitrate-Induced Relaxation of Hemoglobin and by Methylene Blue in the Rabbit Aorta,"*The Journal of Pharmacology and Experimental Therapeutics*, 232(3):708–716, 1985, published in USA.

Buga et al., "Endothelium-Derived Nitric Oxide Relaxes Nonvascular Smooth Muscle, " *European Journal of Pharmacology*, 161:61–72, 1989, published in Europe.

Stuehr et al., "Synthesis of Nitrogen Oxides from L-Arginine by Macrophage Cytosol: Requirement for Inducible and Constitutive Components," *Biochemical and Biophysical Research Communications*, 161(2):420–426, 1989, published in USA.

Torti et al., "A Macrophage Factor Inhibits Adipocyte Gene Expression: An In Vitro Model of Cachexia," *Science*, 229:867–871, 1985, published in USA.

Kilbourn et al., "Activated Macrophages Secrete a Soluble Factor that Inhibits Mitochondrial Respiration of Tumor Cells," *The Journal of Immunology*, 133(5):2577–2588, 1984, published in USA.

Vallance et al., "Effects of Endothelium-Derived Nitric Oxide on Peripheral Arteriolar Tone in Man," *The Lancet, Ltd.*, 997–999, 1989, published in the United Kingdom.

Palmer et al., "Vascular Endothelial Cells Synthesize Nitric Oxide from L-arginine," *Nature*, 333:664–666, 1988, published in the United Kingdom.

Old, Loyd J., "Tumor Necrosis Factor (TNF)," *Science*, Science, 230:630–632, 1985, published in USA.

Yoshida, Katsumi and Kasama, Kazuo, "Biotransformation of Nitric Oxide," *Environmental Health Perspectives*, 78:201–206, 1987, published in USA.

Reif, David W., and Simmons, Roy D., "Nitric Oxide Mediates Iron Release from Ferritin," *Archives of Biochemistry and Biophysics*, 283(2):537–541, 1990, published in USA.

Kruszyna et al., "Nitrite Conversion to Nitric Oxide in Red Cells and Its Stabilization as a Nitrosylated Valency Hybrid of Hemoglobin," *The Journal of Pharmacology and Experimental Therapeutics*, 241(1):307–313, 1987, published in USA.

Kosaka et al., "The Interaction Between Nitrogen Oxides and Hemoglobin and Endothelium-Derived Relaxing Factor," *Free Radical Biology and Medicine*, 7:653–658, 1989, published in USA.

Chevion et al., "Iron-Nitrosyl Bond Configuration in Nitrosyl-Hemoproteins: A Comparative EPR Study of Hemoglobin A and Hemoglobin Kansas," *Israel Journal of Chemistry*, 15:311–317, 1976, published in Israel.

Collier and Vallance, "Second Messenger Role for NO Widens to Nervous and Immune Systems," *Trends in Pharmacological Sciences including Toxicological Sciences*, Elseview Science Publishers, Ltd., 1989, front page and 428–431, published in the United Kingdom.

Ignarro et al., "Endothelium-derived relaxing factor produced and released from artery and vein is nitric oxide," *Proc. Natl. Acad. Sci. USA*, 84:9265–9269, 1987, published in USA.

Murray, et al., "Stabilization and Partial Characterization of Endothelium-Derived Relaxing Factor from Cultured Bovine Aortic Endothelial Cells," *Biochemical and Biophysical Research Communications*, 141(2):689–696, 1986, published in USA.

Marletta, Michael A., "Nitric Oxide: Biosynthesis and Biological Significance," name of publication unknown, Elseview Science Publishers, Ltd., 488–493, 1989, published in the United Kingdom.

Ohlsson et al. Nature vol. 348 Dec. 6, 1990 pp. 550–552.

Kilbourn et al., (1990), "Endothelial Cell Production of Nitrogen Oxides in Response to Interferon γ in Combination with Tumor Necrosis Factor, Interleukin-1 or Endotoxin," *Journal Nat'l Cancer Inst.*, 82(9):772–776, published in USA.

Kilbourn et al., (May 1990), "$N^G$-Methyl-L-Arginine Inhibits Tumor Necrosis Factor-Induced Hypotension: Implications for the Involvement of Nitric Oxide,"

OTHER PUBLICATIONS

*Proc. Natl. Acad. Sci. USA*, 87:3629–32, published in USA.

Sakuma et al., (1988), "Identification of Arginine As A precursor of Endothelium-Derived Relaxing Factor," *Proc. Natl. Acad. Sci. USA*, 85:8664–67, published in USA.

Stuehr et al, (1989), "Activated Murine Macrophages Secrete a Metabolite of Arginine with the Bioactivity of Endothelium-Derived Relaxing Factor and the Chemical Reactivity of Nitric Oxide," *J. Exp. Med.*, 169:1011–20, published in USA.

Hibbs et al., (1988), "Nitric Oxide: A Cytotoxic Activated Macrophage Effector Molecule," *Biochem. Biophys. Res. Comm.*, 157(1): 87–94, published in USA.

Stuehr et al., (1987), "Induction of Nitrite/Nitrate Synthesis in Murine Macrophages by BCG Infection, Lymphokines, or Interferon-$\gamma^1$," *J. Immunology*, 139:518–525, published in USA.

Palmer et al., (1987), "Nitric Oxide Release Accounts for the Biological Activity of Endothelium-Derived Relaxing Factor," *Nature*, 327:524–526.

Natanson et al., (1989), "Endotoxin and Tumor Necrosis Factor Challenges in Dogs Simulate the Cardiovascular Profile of Human Septic Shock," *J. Exp. Med.*, 169:823–832, published in USA.

Starnes et al., (1988), "Tumor Necrosis Factor and the Acute Metabolic Response to Tissue Injury in Man," *J. Clin. Invest.*, 82(4):1321–1325, Dialog Search Report Abstract, published in USA.

Nathan et al., (1990), "Does Endotherlium-Derived Nitric Oxide Have a Role in Cytokine-Induced Hypotension?" *J. Natl. Cancer Inst. USA*), 82(():726–728, Dialog Search Report Abstract, published in USA.

Schmidt et al., (1988), "Arginine Is a Physiological Precursor of Endothelium-Derived Nitric Oxide," *European J. of Pharmacology*, 154:213–216, published in Europe.

Dialog Search Report, printed in USA.

Carter et al., (1990), "Purification, Cloning, Expression and Biological Characterization of an Interleukin-1 Receptor Antagonist Protein," *Nature*, 344:633–638, published in United Kingdom.

Hannum et al., (1990), "Interleukin-1 Receptor Antagonist Activity of a Human Interleukin-1 Inhibitor," *Nature*, 343:336–340, published in United Kingdom.

Eisenberg et al., (1990), "Primary Structure and Functional Expression from Complementary DNA of a Human Interleukin-1 Receptor Antagonist," *Nature*, 343:341–346, published in United Kingdom.

Teng et al., (1985), "Protection Against Gram-Negative Bacteremia and Endotoxemia with Human Monoclonal IgM Antibodies," *Proc. Natl. Acad. Sci. USA*, 82:1790–1794, published in USA.

Bone, Roger C., (1991), "A Critical Evaluation of New Agents for the Treatment of Sepsis," *JAMA*, 266(12):1686–1690, published in USA.

Ziegler et al., (1991), "Treatment of Gram-Negative Bacteremia and Septic Shock with HA-1A Human Monoclonal Antibody Against Endotoxin," *New England Journal of Medicine*, 324(7):429–436, published in USA.

Wakabayashi et al., (1991), "A Specific Receptor Antagonist for Interleukin 1 Prevents *Escherichia coli*-Induced Shock in Rabbits," *The FASEB Journal*, 5:336–343, published in USA.

Baumgartner et al., (1990), "Association Between Protective Efficacy of Anti-Lipopolysaccharide (LPS) Antibodies and Suppression of LPS-Induced Tumor Necrosis Factor $\alpha$ and Interleukin 6: Comparison of O Side Chain-Specific Antibodies with Core LPS Antibodies," *J. Exp. Med.*, 171:889–896, published in USA.

Calandra et al., (1991), "Anti-Lipopolysaccharide and Anti-Tumor Necrosis Factor/Cachectin Antibodies for the Treatment of Gram-Negative Bacteremia and Septic Shock," *Bacterial Endotoxins: Cytokine Mediators and New Therapies for Sepsis*, pp.:141–159, place of publication is unknown.

Calandra et al., (1988), "Treatment of Gram-Negative Septic Shock with Human IgG Antibody to *Escherichia coli* J5: A Prospective, Double-Blind, Randomized Trail," *Journal of Infectious Diseases*, 158(2):312–319, published in USA.

Opal et al., (1991), "Efficacy of Antilipopolysaccharide and Anti-Tumor Necrosis Factor Monoclonal Antibodies in a Neutropenic Rat Model of *Pseudomonas Sepsis*," *J. Clin. Invest.*, 88:885–890, published in USA.

Wolff, Sheldon M., (1991), "Monoclonal Antibodies and the Treatment of Gram-Negative Bacteremia and Shock," *The New England Journal of Medicine*, 324(7):486–488, published in USA.

Kilbourn, Robert G. and Griffith, Owen W., (1992), "Overproduction of Nitric Oxide in Cytokine-Mediated and Septic Shock," *Journal of the National Cancer Institute*, 84(11):827–831, published in USA.

OTHER PUBLICATIONS

Kilbourn et al., (1992), "Inhibition of Interleukin-1-α-Induced Nitric Oxide Synthase in Vascular Smooth Muscle and Full Reversal of Interleukin-1-α-Induced Hypotension by Nω-Amino-L-Arginine," *Journal of Nat'l Cancer Institute*, 84(13):1008–1016, galley proof provided, published in USA.

Kilbourn et al., (1990), "Reversal of Endotoxin-Mediated Shock by $N^G$-Methyl-L-Arginine, an Inhibitor of Nitric Oxide Synthesis," *Biochemical and Biophysical Research Communications*, 172(3):1132–1138, published in USA.

Exley et al., (1990), "Monoclonal Antibody to TNF in Severe Septic Shock," *The Lancet*, 335:1275–1277, published in Great Britain.

Hibbs et al., (1987), "L-Arginine is Required for Expression of the Activated Macrophage Effector Mechanism Causing Selective Metabolic Inhibition in Target Cells," *J. Immunology*, 138:550–565, published in USA.

Palmer et al., (1988), "L-Arginine is the Physiological Precursor for the Formation of Nitric Oxide in Endothelium-Dependent Relaxation," *Biophysical and Biophysical Research Communications*, 153(3):1251–1256, published in USA.

Sun et al., (1990), "Effects of *In Vivo* 'Priming' on Endotoxin-Induced Hypotension and Tissue Injury," *American Journal of Pathology*, 136(4):949–956, published in USA.

Marks et al., (1990), "Plasma Tumor Necrosis Factor in Patients with Septic Shock," *Am. Rev. Respir. Dis.*, 141:94–97, published in USA.

Silva et al., (1990), "Monoclonal Antibody to Endotoxin Core Protects Mice from *Escherichia coli* Sepsis by a Mechanism Independent of Tumor Necrosis Factor and Interleukin-6," *Journal of Infectious Diseases*, 162:454–459, published in USA.

Silva et al., (1990), "Prophylactic and Therapeutic Effects of a Monoclonal Antibody to Tumor Necrosis Factor-α in Experimental Gram-Negative Shock," *Journal of Infectious Diseases*, 162:421–427, published in USA.

Opal et al., (1990), "Efficacy of a Monoclonal Antibody Directed Against Tumor Necrosis Factor in Protecting Neutropenic Rats from Lethal Infection with *Pseudomonas aeruginosa*," *Journal of Infectious Diseases*, 161:1148–1152, published in USA.

Tracey et al., (1987), "Anti-Cachectin/TNF Monoclonal Antibodies Prevent Septic Shock During Lethal Bacteraemia," *Nature*, 330:662–664, published in United Kingdom.

Aisaka et al., (1989), "$N^G$-Methylarginine, An Inhibitor of Endothelium-Derived Nitric Oxide Synthesis, Is a Potent Pressor Agent in the Guinea Pig: Does Nitric Oxide Regulate Blood Pressure in Vivo," *Biochemical and Biophysical Research Communications*, 160(2):881–886, published in USA.

Rees et al., (1989), "Role of Endothelium-Derived Nitric Oxide in the Regulation of Blood Pressure," *Proc. Natl. Acad. Sci. USA*, 86:3375–3378, published in USA.

ANTI-ENDOTOXIN, INTERLEUKIN-1 RECEPTOR ANTAGONIST AND ANTI-TUMOR NECROSIS FACTOR ANTIBODY WITH ARGININE-FREE FORMULATIONS FOR THE TREATMENT OF HYPOTENSION

The government has rights in the present invention as research relevant to the development thereof was funded by NIH grant DK 37116.

The present application is a continuation-in-part of Ser. No. 767,205, U.S. Pat. No. 5,286,739, filed Sep. 27, 1991, which is specifically incorporated herein by reference.

BACKGROUND OF THE INVENTION

1. Field of the Invention

The present invention relates to the field of methods and compositions for the treatment of hypotension. The invention also relates to the field of combination therapeutic regimens particularly those which include a regimen of a particularly tailored parenteral formulation. The present invention also relates to the field of anti-tumor necrosis factor antibodies, as well as anti-endotoxin antibodies and interleukin-1 receptor antagonists as part of a therapeutic regimen for the treatment of hypotension, septic shock and related conditions.

2. Background of the Related Art

In 1980, Furchgott and Zawadski (Nature 288:373–376) demonstrated that endothelial cells, which line blood vessels, can be stimulated to release a substance which relaxes vascular smooth muscle i.e., causes vasodilatation. Since the chemical nature of this substance was completely unknown, it was simply named endothelium-derived relaxing factor (EDRF). It is now widely accepted that many naturally-occurring substances which act as physiological vasodilators mediate all or part of their action by stimulating release of EDRF; these substances include, acetylcholine, histamine, bradykinin, leukotrienes, ADP, ATF, substance P, serotonin, thrombin and others.

Although the extremely short lifetime of EDRF (several seconds) hampered efforts to chemically identify this molecule, in 1987 several laboratories suggested that EDRF may be nitric oxide (NO). Nitric oxide is known to spontaneously decompose to nitrate and nitrite. A fundamental problem in accepting this NO hypothesis was that mammalian systems were not known to contain an enzymatic pathway which could synthesize NO; additionally, a likely precursor for NO biosynthesis was unknown. After observing that the arginine analog L-$N^G$-methylarginine (L-NMA) could inhibit vascular EDRF/NO synthesis induced by acetylcholine and histamine, and that EDRF/NO synthesis could be restored by adding excess L-arginine, certain of the present inventors proposed that arginine is the physiological precursor of EDRF/NO biosynthesis (Sakuma et al. (1988), PNAS, 85:8664–8667). Certain of the present inventors later demonstrated that inhibition of EDRF/NO synthesis in the anesthetized guinea pig raises blood pressure (Aisaka et al. (1989), BBRC 160:881–886). This information further suggested to the inventors that EDRF/NO was an important physiological regulator of blood pressure.

Other laboratories have reported that macrophage cells become "activated" by 12–36 hour treatment with gamma-interferon, bacterial endotoxin and various cytokines. This "activation" is associated with initiation of tumor cell killing and generation of nitrite and nitrate from L-arginine. It was observed that activated macrophages actually make NO from L-arginine (just like endothelial cells) and that this NO subsequently reacts with oxygen to form more oxidized nitrogen metabolites which appear to be physiologically inert (Stuehr et al. (1989), J. Exp. Med. 169:1011–1020).

Cytokines are well known to cause morphological and functional alterations in endothelial cells. These alterations occur in part as a result of "endothelial cell activation" Distinct immune-mediators such as tumor necrosis factor (TNF), interleukin-1 (IL-1), and gamma-interferon (IFN) appear to induce different but partially overlapping patterns of endothelial cell activation including increased procoagulant activity (Bevilaqua (1986) PNAS, 83:4533–4537), PGI and 2 production (Rossi (1985), Science, 229:174–176), HLA antigen expression (Pober (1987) J. Immunol., 138:3319–3324) and lymphocyte adhesion molecules (Carender (1987) J. Immunol., 138:2149–2154). Although these cytokines are reported to cause hypotension, vascular hemorrhage, and ischemia, the underlying mechanisms of altered vasoactivity are unclear (Goldblum et al. 1989, Tracey et al. Science 234:470, 1986). A potential mediator of altered vasoactivity proposed by the present inventors is EDRF. A major dose limiting toxicity of these and other biological response modifiers is hypotension and vascular leakage (Dvorak (1989) J.N.C.I., 81:497–502). Thus, the clinical utility of these and other agents remains limited. A method for providing the therapeutic effects of these agents without the risk of potentially lethal side effects before the practical and widespread utilization of these agents can be realized by the medical community.

Septic shock, a life-threatening complication of bacterial infections, affects 150,000 to 300,000 patients annually in the United States (Parrillo, J. E. (1989), Septic Shock in Humans: Clinical Evaluation, Pathogenesis, and Therapeutic Approach (2nd ed.) In: Textbook of Critical Care. Shoemaker, et al., editors, Saunders Publishing Co., Philadelphia, Pa., pp. 1006). The cardiovascular collapse and multiple metabolic derangements associated with septic shock are due largely to bacterial endotoxin (ET), which has been shown to elicit a septic shock-like condition when administered to animals (Natanson, et al. (1989), Endotoxin and Tumor Necrosis Factor Challenges in Dogs Simulate the Cardiovascular Profile of Human Septic Shock, J. Exp. Med. 169:823).

ET is known to stimulate the synthesis and release of several cytokines and biological mediators having hypotensive activity. Among the factors released, TNF, PAF, prostacyclin and complement-derived C5a anaphylatoxin have been proposed as important contributors to the cardiovascular collapse of septic shock (Hesse, et al. (1988), Cytokine Appearance in Human Endotoxemia and Primate Bacteremia, Surg. Gynecol. Obstet., 166:147; Etienne, et al. (1986), The Relative Role of PAF-acether and Icosanoids in Septic Shock, Pharmacol. Res. Commun., 18:71; Halushka, et al. (1985), Elevated plasma 6-keto-prostaglandin F1 alpha in Patients in Septic Shock, Crit. Care Med., 13:451; Smedegard, et al. (1989), Endotoxin-induced Shock in the Rat: A Role for C5a, Am. J. Pathol., 135:489). It has been shown that animals pretreated with anti-TNF antibodies (Beutler et al. (1985), Passive immunization against cachectin/TNF protects mice from lethal effects of ET, Science, 229:869), PAF receptor antagonists (Casals-Stenzel (1987), Protective Effect of WEB 2086, a Novel Antagonist of Platelet Activating Factor in Endotoxin Shock, European J. Pharmacology, 135:117), and prostacyclin synthesis inhibitors (Wise, et al. (1985), *Ibuprofen, Methylprednisolone, and Gentamycin as Cojoint Therapy in Septic Shock, Circ. Shock,* 17:59) are protected against septic shock. However, the relative importance of these mediators in the pathology of septic shock is presently uncertain, which in turn renders them unpredictable for widespread clinical use, There is also evidence that some of these mediators may act indirectly via release of secondary mediators, in direct support of the finding that anti-TNF antibodies have little or no protective effect when given after ET exposure (Beutler, et al. (1985) *Science,* 229:8691).

The pathogenesis of the cardiovascular collapse that occurs during septic shock is poorly understood. Current treatment includes i.v. fluid administration and use of pressor drugs to increase peripheral vascular resistance and maintain organ perfusion. Very recently, endotoxin-binding agents including polymyxin B (Hanasawa, et al. (1989), *New Approach to Endotoxic and Septic Shock by Means of Polymyxin B Immobilized Fiber, Surg. Gynecol. Obstet.* 168:232) and antibodies which neutralize TNF (Tracey, et al. (1987), *Anti-cachectin/TNF monoclonal antibodies prevent septic shock during lethal bacteremia, Nature,* 330:662–664) have been used in an attempt to modify the sequelae of septic shock. The latter approach may have prophylactic value. However, no evidence exists that such an approach would be useful in reversing septic shock. The present inventors propose that therapy of patients already in septic shock requires intervention at secondary and tertiary steps in the cascade of events initiated by endotoxin.

The development of hypotension and other changes associated with septic shock may depend on complex interactions between cytokines, eicosanoids, PAF, activated complement components, and other factors. It is, therefore, not surprising that several interventions have been found to be at least partially effective in some models.

Increased circulating nitrogen oxides following interleukin-2 (IL-2) immunotherapy has been shown by Ochoa (1992) (*J.N.C.I.,* 84:864–867). Ochoa et al. (J. Natl. Cancer Inst., 84:864–867 (1992)) have also shown that plasma nitrate levels are elevated about nine-fold in cancer patients receiving IL-2- and anti-CD3-activated lymphocytes. This increase in plasma nitrates correlated temporarily and quantitatively (albeit loosely) with the systemic hypotension characteristic of IL-2 administration. Although significant nitrate is present in a normal diet., Ochoa et al. assert that the increased plasma nitrate seen in anorexic patients reflects the overproduction of NO. by IL-2-induced nitric oxide synthase. Hibbs et al. (J. Clin. Invest. 89:867–877 (1992)) achieved even greater verification of this point by showing the conversion of [$^{15}$N]arginine to [$^{15}$N]nitrate. The possible contribution of decreased renal function to the observed increases in plasma nitrate was shown to be minimal (Ochoa (1992)). These studies and recently reported similar studies by Hibbs et al. ((1992) *J. Clin. Invest.,* 89:867–877) definitively show cytokine-mediated induction of NO. synthesis in humans.

The findings of Ochoa et al. and Hibbs et al. described provide strong support for the view that the dose-limiting hypotension associated with the therapeutic use of IL-2 in humans is mediated by NO.. The studies also accord well with earlier studies by Wagner's group (PNAS (1983), 80:4518–4521), indicating that plasma and urinary nitrate levels increase in endotoxemic animals, an effect now attributable to the endotoxin-mediated induction of nitric oxide synthase (Ochoa et al. (1991) Ann. Surg., 214:621–626). It is notable that the findings in IL-2-induced hypotension and in septic shock are mechanistically related, since both IL-2 and endotoxin induce synthesis of IL-1 and tumor necrosis factor (Gento et al. (1988); Boccoli et al. (1990); Cancer Res. 50:2371–2374 (1990)), and that those cytokines have been shown to induce nitric oxide synthase in several systems (Kilbourn et al. (1990), *PNAS,* 87:3629–3632; Busse et al. (1990) FEBS Letts., 275:87–90; Kilbourn et al. (1990) J. Natl. Cancer Inst. 82:172–176).

While a variety of parenteral formulations have been described in the literature, some of which are compositionally modified so as to exclude arginine, none have been described for use in conjunction with anti-tumor necrosis factor antibodies, anti-endotoxin antibodies, or IL-1 receptor antagonists. Instead, formulations specially tailored for cancer patients to be used as a therapy for inhibiting tumor growth, such as those described by Ajani et al. are present in the art. Arginine-free parenteral formulations have not been described as part of a combination therapy, particularly in a therapeutic regimen or method for the treatment of hypotension.

The considerations outlined above suggest that therapeutic approaches to NO.-mediated shock should (a) target the inducible isoform of nitric oxide synthase, (b) accommodate the ready and unregulated diffusion of NO., and (c) if possible, be particularly effective in limiting NO. production by vascular endothelium and smooth muscle. The present invention provides approaches which meet all of these goals with combination therapies that may be useful in the management of pathologies and conditions where hypotension and septic shock present a health risk.

SUMMARY OF THE INVENTION

The inventors herein propose uses of anti-TNF antibodies, anti-endotoxin antibodies, and cytokine receptor antagonists (e.g., IL-1 receptor antagonist) in combination with arginine-free formulations in conceptually distinct approaches for the treatment of septic and cytokine-induced shock. The arginine-free formulations may be conveniently supplied as either a parenteral formulation (to be administered intravenously) or as an oral formulation (to be administered enterally). The most preferred embodiment of the parenteral formulation comprises a parenteral formula.

Since antibodies and receptor antagonists intervene early in the pathological response to cytokines, their optimal use requires anticipation of shock. While administration of these agents could affect important biological events after the initiation of the biological response to endotoxin or cytokines, these agents do not block NO synthesis once the enzyme is induced. Because NO production, once induced in smooth muscle cells, appears to persist for more than 16 hours after transfer to cytokine-free medium, antibodies and receptor antagonists are less likely to be effective at blocking or slowing NO synthesis once it has begun. The recently reported potential benefit of a human monoclonal antibody against endotoxin in patients with septic shock associated with gram-negative bacteremia (Ziegler et al. (1991) *New England Journal of Medicine,* 324:429) is best attributed to the prevention of further induction of cytokine mediators rather than to direct improvement of the existing cardiovascular profile. In contrast, the inventors own work has demonstrated that nitric oxide synthase inhibitors or treatments designed to act to limit nitric oxide synthase substrate availability, act within minutes, even in severe shock.

The rapidity of the response to nitric oxide synthase inhibitors and to treatments designed to limit nitric oxide synthase substrate availability, and the fact that their efficacy is independent of the precipitating factor (i.e., endotoxin, TNF, IL-1 or IL-2) are important clinical considerations that the present inventors have focused in the combination therapies and regimens of the present invention. Antibodies and receptor antagonists, in contrast to nitric oxide synthase inhibitors and substrate depletion strategies, can potentially prevent all of the biological responses to endotoxin or cytokines. This breadth of action is desirable in severe sepsis.

According to one aspect of the present invention, a therapeutic regimen comprising a therapeutically effective amount of an arginine-free formulation to be administered concurrently with or followed by a therapeutically effective amount of an anti-endotoxin antibody is provided. The formulation is further defined as comprising a mixture of essential and nonessential amino acids together in a pharmacologically acceptable excipient while the formulation may be prepared as either a parenteral or enteral formulation; a parenteral formulation is most preferred. The anti-endotoxin antibody may comprise either a polyclonal antibody or a monoclonal antibody. Most preferably, however, the anti-endotoxin antibody is a monoclonal antibody. By way of example, such a monoclonal antibody is HA-1A.

The parenteral formulation of the therapeutic regimen is defined as including: about 3-4 g/l isoleucine, about 4-6 g/l leucine, about 3-4 g/l lysine, about 1-2 g/l methionine, about 1-2 g/l phenylalanine, about 2-3 g/l threonine, about 0.5-1.5 g/l tryptophan, about 3-4 g/l valine, about 4-5 g/l alanine, about 1-2 g/l histidine, about 3-4 g/l proline, about 1-2 g/l serine, about 0.25-0.75 g/l tyrosine, about 4-5 g/l glycine and about 2-3 g/l aspartic acid, together in a pharmacologically acceptable excipient. In another preferred embodiment of the described parenteral formulation, the formulation may further include ornithine, most particularly at a concentration of about 1-2 g/1. In still another embodiment of the described parenteral formulation, the formulation may include citrulline, most preferably at a concentration of between about 1 g/l and about 2 g/l. Both citrulline and ornithine may be included in still another embodiment of the formulation, again at the concentrations indicated.

The pharmacologically acceptable excipient for use in the formulation of the described parenteral formulation is most preferably a Ringer's solution or saline. Of these, saline is the most preferred excipient.

In a most preferred embodiment of the described therapeutic regimen, the parenteral formulation is to be administered concurrently (simultaneously) with the administration of the anti-endotoxin antibody. The therapeutically effective amount of the formulation is most particularly defined as an amount sufficient to reduce plasma or serum concentrations of arginine in the animal. A reduction in plasma or serum concentrations of arginine in the animal is anticipated to be accomplishable by administering to the animal a continuous intravenous feed of the arginine-free formulation as a parenteral intravenous feed for at least 2 hours. It is anticipated that a preferred practice of using the therapeutic regimen will include the administration of the arginine-free formulation concurrently with the administration of the anti-endotoxin antibody. Simultaneous or concurrent administration is preferred primarily due to the need for the various treatments to act so as to provide the most rapid control of the hypotensive condition.

While the anti-endotoxin antibody may be administered to the animal via a number of routes known to those of skill in the medical arts, intravenous administration of the anti-endotoxin antibody is most preferred.

In still another aspect of the present invention, a therapeutic regimen comprising a therapeutically effective amount of an arginine-free formulation administered concurrently with or followed by a therapeutically effective amount of an interleukin-1 receptor antagonist is provided. Again, the parenteral formulation may be described as comprising a mixture of essential and nonessential amino acids together in a pharmacologically acceptable excipient. The parenteral formulation of this therapeutic regimen will include the amino acids and concentrations thereof already recited, and may also include ornithine or citrulline, or both. Where ornithine and/or citrulline is included in the formulation, a concentration of about 1-2 g/l of each agent may be included. Ornithine and citrulline are to be provided in the formulation so as to even further fortify the nutrient value of the formulation to the animal, as well as to assure that adequate metabolic requirements for urea cycle substrates are provided to the animal.

The most preferred route of administration of the interleukin-1 receptor antagonist is via intravenous administration. However, other routes of administration may be used with equally efficacy in the practice of the claims therapeutic regimen. A most particularly preferred interleukin-1 receptor antagonist to be used in the present invention is IL 1ra. Most preferably, the arginine-free parenteral formulation is to be administered concurrently with the interleukin-1 receptor antagonist.

The present invention also includes a therapeutic regimen which comprises a therapeutically effective amount of an arginine-free formulation to be administered concurrently with or followed by a therapeutically effective amount of an anti-tumor necrosis factor antibody. Again, the arginine-free formulation is to comprise a mixture of essential and nonessential amino acids together in a pharmacologically acceptable excipient, and is most preferably to be administered concurrently with the anti-tumor necrosis factor antibody. While the formulation may be either a parenteral or enteral formulation, parenteral formulations are most preferred.

The anti-tumor necrosis factor antibody may comprise either a monoclonal antibody or a polyclonal antibody, with the monoclonal antibody for tumor necrosis factor being most preferred. These antibodies may be prepared according to methods well known to those of skill in the art, including standard immunization protocols and/or hybridoma technologies. Tumor necrosis factor may be obtained from commercial sources for such methods. For example, tumor necrosis factor may be obtained from Amgen Biologicals (Thousand Oaks, Calif.). By way of example, an anti-tumor necrosis factor monoclonal antibody which may be used in the practice of the invention is CB0006, which is described in Exley et al. (1990) Lancet, 335:1275-1277. The Exley et al. reference is specifically incorporated herein by reference for this purpose.

The arginine-free formulation is most preferably to include the mixture of essential and nonessential amino acids described herein, together in a pharmacologically acceptable excipient. In addition, the formulation may further include ornithine and/or citrulline for the reasons aforedescribed. The formulation is most preferably to be prepared so as to be suitable for use/administration as a parenteral formulation.

It is contemplated that the therapeutically effective amount of the anti-tumor necrosis factor antibody to be used in the described therapeutic regimen is about 0.1 mg/kg to about 20 mg/kg. Most preferably, it is anticipated that a therapeutically effective amount of anti-tumor necrosis factor will be provided to the animal at a dose of about 10 mg/kg. The most preferred route of administration of the anti-tumor necrosis factor antibody is via intravenous administration. Most preferably, the parenteral formulation is to be administered concurrently with the administration of the anti-tumor necrosis factor antibody, and in an amount sufficient to reduce plasma or serum concentrations of arginine.

It is contemplated that the amount of arginine-free parenteral formulation which will be sufficient to reduce plasma or serum concentrations of arginine in the animal constitutes an intravenous feed of the arginine-free parenteral formulation as described herein for at least 2 hours. In a preferred aspect of the described therapeutic regimen, the arginine-free parenteral formulation is to be administered concurrently with the administration of the anti-tumor necrosis factor antibody.

The parenteral formulation of the aforedescribed therapeutic regimen is most particularly described as anti-hypotensive in nature, as the formulation is anticipated to result in an overall increase in abnormally low blood pressure levels in an animal to normotensive levels (normotensive is defined as a systolic blood pressure of at least about 100 mm Hg).

In still another aspect of the described invention, a method for treating hypotension attendant to septic shock is provided. The method comprises administering to the animal a therapeutically effective amount of an arginine-free formulation concurrently with or prior to administering a therapeutically effective amount of an anti-endotoxin antibody, periodically monitoring blood pressure in the animal until a systolic blood pressure of at least 100 mm Hg is detectable in the animal, and maintaining the animal on the arginine-free parenteral formulation until a systolic blood pressure of at least 100 mm Hg for at least 24 hours is established. This method is anticipated to be most particularly preferred in the treatment of hypotension attendant that septic shock which is a bacterial endotoxin-related septic shock. The arginine-free formulation is most preferably prepared as a parenteral formulation. It is contemplated that the described method may be useful in the treatment of humans in septic shock.

The anti-endotoxin antibody of the described method may be either a monoclonal antibody or a polyclonal antibody, with monoclonal antibodies to endotoxin being most particularly preferred. By way of example, such an anti-endotoxin monoclonal antibody is designated HA-1A, which is described in detail in the examples included herein. A therapeutically effective concentration of the anti-endotoxin antibody as part of the herein-described method is defined as constituting a concentration of between about 0.1 mg/kg to about 20 mg/kg.

The method includes an arginine-free formulation which comprises the amino acids and concentrations thereof already described herein, together in a pharmacologically acceptable excipient. Again, the formulation may further include ornithine, citrulline, or both, to even further supply physiologically required concentrations of urea cycle substrates in the animal. Most preferably, the formulation is provided as a parenteral formulation, and is to be administered concurrently with the anti-endotoxin antibody.

Another aspect of the method comprises a method for treating chemotherapeutic agent-related hypotension. In a most preferred embodiment, the method comprises monitoring an animal receiving a chemotherapeutic agent for a decrease in systolic blood pressure to less than about 100 mm Hg to detect an animal with systemic hypotension, treating the animal having systemic hypotension with a therapeutic regimen comprising a therapeutically effective amount of an arginine-free formulation sufficient to reduce plasma or serum arginine concentrations administered concurrently with or followed by the administration of a therapeutically effective concentration of an interleukin-1 receptor antagonist or an anti-tumor necrosis factor antibody, and maintaining the animal on the therapeutic regimen until an increase of systolic blood pressure to at least about 100 mm Hg is detectable. Most preferably, the arginine-free formulation is a parenteral formulation. The formulation is most preferably administered concurrently with an antagonist or antibody.

It is contemplated that the described method may be useful in the treatment of a human receiving a chemotherapeutic therapeutic agent associated with the development of hypotension. By way of example, chemotherapeutic agents associated with a decrease in blood pressure, i.e. hypotension, include tumor necrosis factor, interleukin-1 and interleukin-2.

Where the chemotherapeutic agent being administered to the animal is tumor necrosis factor, the therapeutic regimen will include the administration of an interleukin-1 receptor antagonist, such as IL 1ra. In contrast, where the chemotherapeutic agent being used is interleukin-1 or interleukin-2, the therapeutic regimen will include an anti-TNF antibody.

Ordinarily, patients receiving TNF would not preferentially receive anti-TNF antibodies. However, if severe refractory hypotension occurs, then anti-TNF antibody treatment combined with an arginine-free TPN may be useful even where TNF is the chemotherapeutic agent being used. Such constitute potential rescue strategies in treating patients with refractory hypotensive conditions.

Again, the arginine-free parenteral formulation to be used in conjunction with either the interleukin-1 antagonist or anti-tumor necrosis factor antibody includes the amino acids and concentrations thereof already described herein, together in a pharmacologically acceptable excipient. The formulation may also further include ornithine, citrulline, or both, for the reasons described herein. The therapeutically effective concentration of the interleukin-1 receptor antagonist is more particularly defined as constituting a concentration of between about 1 mg/kg to about 100 mg/kg. The anti-tumor necrosis factor antibody most preferred for use in the described method is a monoclonal antibody, and will constitute a therapeutically effective concentration thereof of between about 0.1 mg/kg to about 20 mg/kg.

The present invention also provides a method for treating septic shock-related hypotension in an animal exposed to endotoxin. This method, in one preferred embodiment, comprises treating the animal with a therapeutically effective amount of an arginine-free formulation sufficient to reduce plasma or serum arginine levels in the animal concurrently with an interleukin-1 receptor antagonist or an anti-endotoxin antibody, or both, monitoring the blood pressure of the animal, and maintaining the animal on the arginine-free parenteral formulation until a systolic blood pressure of at least 100 mm Hg is detected. Most preferably, the formulation is a parenteral formulation.

The present invention also provides a method for treating hypotension in an animal with endotoxic related septic shock or cytokine-induced shock. The method comprises administering to an animal a therapeutically effective amount of an arginine-free formulation sufficient to reduce plasma or serum arginine levels in the animal, administering the formulation concurrently with or prior to the administration of a therapeutically effective amount of an anti-tumor necrosis factor antibody, monitoring blood pressure of the animal, and maintaining the animal on the arginine-free formulation until a systolic blood pressure of at least 100 mm Hg is detected. While the anti-tumor necrosis factor antibody may be a monoclonal or a polyclonal antibody, monoclonal antibodies are most preferred. Again, the arginine-free formulation is most preferably a parenteral formulation.

The arginine-free parenteral formulation of the method includes the amino acids and amounts thereof previously described herein together in a pharmaceutically acceptable excipient. Again, the formulation may include ornithine, citrulline, or both, for the reasons discussed herein. It is contemplated that the therapeutically effective amount of the anti-tumor necrosis factor antibody to be used in conjunction with the described method constitutes an amount of between about 0.1 mg/kg to about 20 mg/kg body weight of the animal. Of this range, a dose of about 10 mg/kg of the anti-tumor necrosis factor may constitute the most effective anti-hypotensive dose when used in conjunction with the arginine-free parenteral formulation. So implemented, it is anticipated that the herein described methods may be useful in the treatment of endotoxin-related septic shock or cytokine-induced shock in a human.

While the anti-tumor necrosis factor antibody or interleukin-1 receptor antagonist may be administered to the animal via any route known to those of skill in the medical arts, it is most preferred that these agents be administered intravenously, most preferably as a separate bolus dose to the animal. The aforedescribed method is anticipated to provide a most preferred embodiment for treating cytokine-induced shock in an animal.

Notwithstanding the accumulated evidence supporting synthesis of NO, it is understood by those skilled in the art that other nitrogen oxides may be present and may be active in reducing blood pressure. Within this specification, the acronym NO. will be understood to represent nitric oxide and any additional vasoactive nitrogen oxides.

The following abbreviations are used throughout the description of the present invention.
ACh=acetylcholine
BAEC=bovine aortic endothelial cells
B.P.=blood pressure
CO=Cardiac output
EDRF=Endothelium-Derived Relaxing Factor
ET=endotoxin
GP=guinea pig
HIST=histamine
IFN=interferon
IL 1ra=interleukin-1 receptor antagonist
ILF=interleukin factor
INF=tumor necrosis factor
IV=Intravenous
L-Arg=L-arginine
LPS=lipopolysaccharide (endotoxin)
MAP=mean arterial pressure
MBEC=murine brain endothelial cells
NE=norepinephrine
NO.=Nitric Oxide
NAA=$N^\omega$-L-amino-L-arginine
L-NMA=L-NMMA=$N^\omega$-methyl-L-arginine
NNA=$N^\omega$-nitro L-arginine
PAF=Platelet Activating Factor
PPS=Platelet—poor, plasma-derived serum
SAP=Systemic arterial pressure
SNP=sodium nitroprusside
SVR=Systemic vascular resistance
TNF=Tumor Necrosis Factor
TPN=Total Parenteral Nutrition Formulation

DETAILED DESCRIPTION OF THE PREFERRED EMBODIMENTS

Figure 1A:
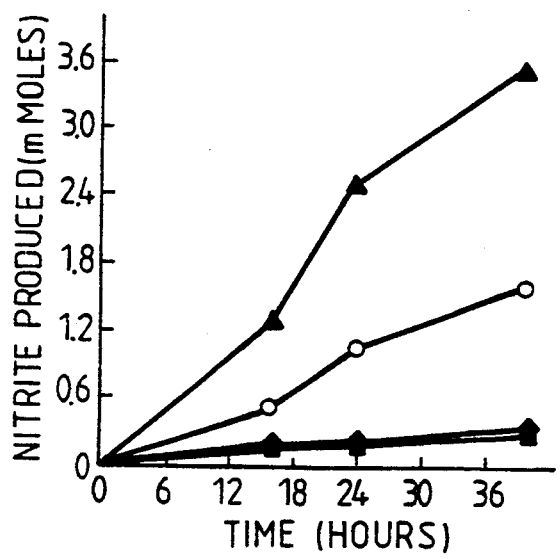
FIG. 1—IL-1 activates nitrite production by rat aortic smooth muscle cells in culture. Panel A: Time course of nitrite synthesis elicited by 40 ng/mL IL-1 alone (open circles) and by IL-1 in the presence of 50 ng/ml IFN-$\gamma$ (open triangles). In the absence of IL-1, IFN-$\gamma$ did not elicit nitrite production. Inclusion of IL-1 receptor antagonist (40 $\mu$g/mL; filled symbols) in the culture medium inhibited nitrite production stimulated by both IL-1 and IL-1 plus IFN-$\gamma$. Panel B: IL-1 concentration dependence for smooth muscle cell nitrite production. Data points indicate nitrite produced during a 29-hour incubation with the indicated concentration of IL-1 alone (open circles) or in the presence of IL-1 plus 50 ng/mL IFN-$\gamma$ (open triangles). All values are means $\pm$SD for nitrite production by confluent smooth muscle cell monolayers grown in 96-well microtiter plates (60–80$\times$10$^3$ cells per well; n=3–4).
Figure 1B:
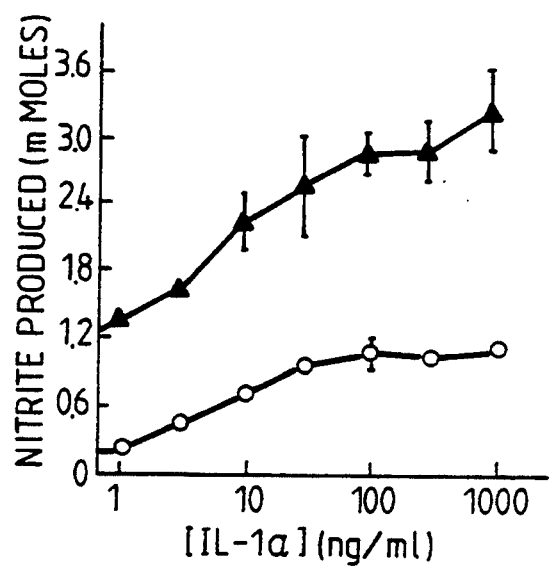

The therapeutic regimens and methods described herein by the inventors provide a novel and potentially more effective method for treating a variety of conditions where hypotension is a typical consequence. For example, hypotension is typically seen in patients suffering from septic shock and in those receiving certain chemotherapeutic agents (TNF, interleukin-1, interleukin-2). The innovative combination of an arginine-free parenteral formulation together with anti-endotoxin antibodies, anti-tumor necrosis factor antibodies, and/or interleukin-1 receptor antagonist may allow for the use of chemotherapeutic agents without the risk of the development of life-threatening hypotension in the animal.

The arginine-free parenteral formulation described may be administered either concurrently with or prior to the administration of the anti-endotoxin antibody, the anti-TNF antibody, or the interleukin-1 receptor antagonist. Most preferably, however, the arginine-free parenteral formulation is administered concurrently with the aforedescribed agents, and may provide for a reduction in serum or plasma arginine levels in the animal so as to preclude substrate availability for the synthesis of nitric oxide, a potent hypotensive agent. In so doing, the present inventors provide a method whereby relatively small amounts of the various antibodies and antagonists may be used to effect a profound normotensive result in the animal.

Recombinant IL-1 or TNF may be obtained from Amgen (Thousand Oaks, Calif.) and used in standard immunization techniques to provide polyclonal antibodies to these antigens. Alternatively, spleen or other tissue from the immunized animals may be used to prepare hybridoma cell lines when fused with an immortal cell line. Such hybridomes constitute a source of monoclonal antibodies specific for their respective antigens.

For purposes of describing the present therapeutic regimens and methods for the treatment of hypotension, such as in a patient or animal with systemic sepsis, the following symptoms will be monitored: fever or hypothermia (temperature >38.3° C. [101° F.] or <35.6° C. [96° F.]; tachycardia (>90 beats per minute in the absence of beta-blockade) and tachypnea (respiratory rate >20 breaths per minute or the requirement of mechanical ventilation); and either hypotension (systolic blood pressure ≦90 mm Hg or a sustained drop in systolic pressure ≧40 mm Hg in the presence of an adequate fluid challenge and the absence of antihypertensive agents) or two of the following six signs of systemic toxicity or peripheral hypoperfusion: unexplained metabolic acidosis (pH ≦7.3 base deficit of >5 mmol per liter, or an elevated plasma lactate level); arterial hypoxemia (partial pressure of oxygen ≦75 mm Hg or ratio of the partial pressure of oxygen to the fraction of inspired oxygen <250); acute renal failure (urinary output of less than 0.5 ml per kilogram of body weight per hour); elevated prothrombin or partial-thromboplastin time or reduction of the platelet count to less than half the base-line value or less than 100,000 platelets power cubic millimeter; sudden decrease in mental acuity; and cardiac index of more than 4 liters per minute per square meter of body-surface area with systemic vascular resistance of less than 800 dyn sec cm$^{-5}$.

The following examples are presented to describe the best invention and are not meant to limit the present invention unless otherwise stated in the claims appended hereto.

EXAMPLE 1

ANTI-HYPOTENSIVE ARGININE-FREE TPN FORMULATION

The present example defines an anti-hypotensive TPN formulation of the present invention. This arginine-free formulation is intended to be used to reduce plasma, serum and/or tissue arginine levels in an animal. The reduced arginine levels in the animal will then augment the anti-hypotensive effect of the anti-TNF antibodies, anti-endotoxin antibodies and interleukin-1 receptor antagonists described herein. This combination therapy can thus be used in the treatment of conditions where hypotension is the sole or an attendant symptom. For example, this regimen may be used in the treatment of an animal in septic shock (exposed to endotoxin), an animal treated with a chemotherapeutic agent associated with reduced blood pressure, or an animal which is generally experiencing hypotension due to trauma.

A sterile, non-pyrogenic, stable solution for parenteral administration to a patient having hypotension or at risk of hypotension or systemic shock, particularly those receiving immunomodulatory agents, is prepared from pure crystalline amino acids, which are dissolved in a glucose solution (5% to 20%) in the following concentrations to provide a 2× concentrate TPN or a ready-to-feed TPN formulation, as indicated:

TABLE 1

| Amino Acids | 2× concentrate mg/100 ml formulation | Final Concentration (Feeding Formulation) g/l |
| --- | --- | --- |
| isoleucine | 600–800 | 3–4 |
| leucine | 800–1200 | 4–6 |
| valine | 600–800 | 3–4 |
| phenylalanine | 200–400 | 1–2 |
| methionine | 200–400 | 1–2 |
| lysine | 600–800 | 3–4 |
| histidine | 200–400 | 1–2 |
| threonine | 400–600 | 2–3 |
| tryptophan | 100–300 | 0.5–1.5 |
| tyrosine | 50–150 | 0.25–0.75 |
| alanine | 800–1000 | 4–5 |
| aspartic acid | 400–600 | 2–3 |
| glycine | 800–1000 | 4–5 |
| proline | 600–800 | 3–4 |
| serine | 200–400 | 1–2 |

To obtain the preferred TPN formulation concentration suitable as a feeding formulation, a volume of 500 ml of the 2× concentrate (defined in Table 1) is mixed with 500 ml of a 50% 35 dextrose solution, for the production of 1 liter of the feeding formulation (i.e., 500 cc of a 2× concentrate of AA and 500 cc of dextrose solution). Most preferably, the dextrose solution is supplemented with a physiologically acceptable concentration of vitamins and minerals.

The TPN of the present methods may also include glutamic acid (400–600 mg/100 ml of a 2× conc., or 2–3 g/l in a final concentration) and/or taurine (50–100 mg/100 mls. of a 2-fold concentrate; 0.25–0.5 g/l final concentration).

The solution is then filter sterilized into appropriate containers for intravenous fluids. To prepare for administration, the volume is then brought to the desired feeding solution concentration with an equal volume of sterile glucose solution. The TPN as a ready to feed formulation is then to be kept cool. The solution may then be administered to a patient intravenously (IV). The pH of the TPN solution must also be adjusted to a physiologically acceptable pH, between 7.0 and 7.4. The formulation is arginine-free.

EXAMPLE 2

CORRELATION BETWEEN SERUM ARGININE LEVELS AND BLOOD PRESSURE IN VIVO

The present example is provided to demonstrate the correlation between plasma arginine levels and blood pressure. More specifically, the present example demonstrates a correlation between low plasma arginine levels and increased blood pressure in endotoxin-treated hypotensive animals.

The present example also demonstrates the utility for employing a parenteral formulation which is essentially arginine free or low enough in arginine to lower plasma arginine levels, to prevent or alleviate synthesis of nitric oxide, which in turn is shown to result in an increase in blood pressure. Maintenance of an animal on an arginine-free parenteral formulation and an anti-TNF antibody, anti-endotoxin antibody or an interleukin-1 antagonist or a combination thereof, would therefore, according to the present invention, provide a method for even further augmenting the anti-hypotensive effect of both components of such a regimen. It is anticipated that significantly higher doses of these agents would otherwise be required in animals with normal or high physiological concentrations of arginine to elicit a normotensive effect. The onset of life-threatening levels of low blood pressure, such as that typically attendant to cytokine-induced hypotension and septic shock may thus be prevented or alleviated in an animal.

The enzyme arginase was used to reduce plasma arginine levels in Sprague-Dawly rats (Weight per rat=250–300 gm). Arginase is an enzyme that converts L-arginine to L-ornithine+urea. The rats were anesthetized with ethyl ether and then pithed as described Shiply and Tilden ((1947), Proc. Soc. Exp. Biol. Med., 65:453–455). The animals were pithed prior to use in the present study so as to eliminate any neurological control of blood pressure.

Arginase was dissolved in sterile saline (1000 I.U./ml) and was administered by intravenous infusion at a rate of 300 I.U./min. for 20 min. One I.U. is the amount of arginase that converts 1 μmol of arginine to products per minute. Blood pressure was determined using a pressure transducer connected to an indwelling catheter placed in the carotid artery as described (Aisaka et al. (1989) BBRC, 160:881–886).

Serum arginine concentrations

The administration of arginase to pithed rats with or without exposure to endotoxin (15 mg/kg dose, ip), according to the dose outlined above, resulted in a decrease in plasma arginine levels of from 150 μM to <4 μM within a few minutes. Plasma arginine remained at levels <4 μM for at least 1 hour after the arginase infusion was stopped.

Blood pressure recording in the pithed rat

To record blood pressure, a tracheotomy was first performed on each rat, after which the rats were artificially respired with room air. The left common carotid artery was then cannulated in each rat for blood pressure measurement via a Statham pressure transducer (Hato Rey, P.R.) and displayed on a physiogram (Grass Instruments, Quincy Mass.). Heart rate was measured from the lead III electrocardiogram.

Two separate groups of animals were examined. The first group of animals, designated the "control" group, received no endotoxin. The blood pressure of the "control" group animals was measured at two different times, once before the administration of arginase and once after the administration of arginase.

The second group of animals, designated the endotoxin group, received a single dose of endotoxin of 15 mg/kg body weight, which was administered at least 6 hours prior to any subsequent arginase treatment. The blood pressure of all animals in both treatment groups was then measured at two different times, again once before arginase treatment and once after arginase treatment.

The results from this example are presented in Table 1.

TABLE 1

EFFECT OF REDUCED PLASMA ARGININE ON BLOOD PRESSURE

| | No Arginase | | Arginase | |
|---|---|---|---|---|
| | B.P. (mm Hg) | Average B.P. | B.P. (mm Hg) | Average |
| Control Rats | | | | |
| 1 | 61 | 59.8 ± 1.3 | 61 | 63.25 |
| 2 | 60 | | 60 | |
| 3 | 60 | | 64 | |
| 4 | 58 | | 68 | |
| Endotoxic Rats (15 mg/Kg) | | | | |
| 1 | 36 | 33.2 ± 3.3 | 44 | 38.4 |
| 2 | 34 | | 40 | |
| 3 | 28 | | 28 | |
| 4 | 32 | | 36 | |
| 5 | 36 | | 44 | |

Blood pressure readings for 4 control pithed rats were 61, 60, 60, and 58 mm Hg (average 59.8±1.3 mm Hg) (See Table 1). Following administration of arginase, blood pressure was unchanged in two rats and increased by 4 and 10 mm Hg in 2 other rats (average increase 3.5±4.7 mm Hg, not statistically significant).

Blood pressure readings for 5 rats at 6 hours after giving 15 mg/kg lipopolysaccharide (endotoxin) by intravenous injection was 36, 34, 28, 32, and 36 mm Hg (average 33.2±3.3 mm Hg, See Table 1). Note that the endotoxin-treated rats were clearly hypotensive relative to the controls.

Following administration of arginase, blood pressure in the endotoxin-treated rats increased by 8, 6, 0, 4, and 8 mm Hg (average increase 5.2±3.3 mm Hg). The average blood pressure increase following arginase treatment of the endotoxic, pithed rats was 15.7% (statistically significant, p<0.05).

Overall, this study shows that reducing plasma arginine levels has no significant effect on blood pressure in control animals, but did have a significant effect on blood pressure readings in endotoxic animals. The lack of a demonstrated effect in control animals may be due to the slow rate of NO. formation in control animals, so as to negate any requirement for exogenous (i.e. plasma) arginine. Thus, a reduction in plasma arginine levels in such animals would not be a limiting factor for generating NO..

In contrast, the rate of NO. formation in endotoxic animals is much faster than in control (non-endotoxic animals), and results in the development of hypotension. In these endotoxic animals, the cells making NO. must obtain extra arginine from the plasma. When plasma arginine is very low in endotoxic animals (i.e. after arginase administration), there is not enough arginine available to sustain a pathologically high rate of NO. synthesis by cells associated with blood vessel walls (i.e., endothelial cells). Thus, the concentration of NO. is reduced, resulting in a concomitant reduction in the level of blood pressure reduction in the vasculature of the animal. Thus, depletion of serum arginine levels could be used to effect an increase in blood pressure in hypotensive animals.

Use of arginine-free TPN solutions, or solutions sufficiently low in arginine concentration so as to effect a sufficient reduction in plasma arginine levels adequate to limit nitric oxide synthesis, for example, to about 4 μM arginine or less (i.e., 4 nM arginine/ml serum arginine), are expected to have a beneficial effect comparable to that of arginase administration for preventing or treating hypotension, particularly hypotension in animals in septic shock.

The arginine-free parenteral formulation of the described therapeutic regimen may be defined further as including a mixture of essential and nonessential amino acids comprising about 3-4 g/l isoleucine, about 4-6 g/l leucine, about 3-4 g/l lysine, about 1-2 g/l methionine, about 1-2 g/l phenylalanine, about 2-3 g/l threonine, about 0.4-1.4 g/l tryptophan, about 3-4 g/l valine, about 4-5 g/l alanine, about 1-2 g/l histidine, about 3-4 g/l proline, about 1-2 g/l serine, about 0.24-0.75 g/l tyrosine, about 4-5 g/l glycine and about 2-3 g/l aspartic acid. Again, the parenteral formulation of the therapeutic regimen is arginine-free. The pharmacologically acceptable excipient of the parenteral formulation is most preferably a Ringers solution or saline. Of these, saline is the most preferred excipient.

The formulation may also optionally include ornithine at a concentration of about 1-2 g/l, as well as citrulline.

EXAMPLE 3

PREPARATION OF ANTI-ENDOTOXIN ANTIBODIES

The present example is provided to demonstrate a proposed method for preparing anti-endotoxin antibodies to be used in the herein described combination therapeutic regimens and methods with an arginine-free parenteral formulation.

Polyclonal antibodies to endotoxin may be prepared through use of an immunization protocol, wherein an animal, for example a mouse, may be injected with a commercial preparation of endotoxin in an amount sufficient to establish anti-endotoxin antibody titer levels in the animal. By way of example, a commercial source of endotoxin may be obtained from Sigma Chemical Co. (St. Louis, Mo.). Endotoxin includes a polypeptide which is common to both gram negative bacterial and *Esceriachia coli* cell wall materials.

HA-1A (Centoxin) is a human monoclonal IgM antibody that binds to the lipid A domain of endotoxin and is produced by the stable heteromyeloma cell line A6(H4C5) developed by Teng, Kaplan, and Braude. (Teng et al. Proc. Natl. Acad. Sci. U.S.A. 82:1790-4, 1985). The Teng et al. reference is specifically incorporated herein by reference for this purpose. HA-1A has been shown to bind specifically to many endotoxins and to a broad range of clinical isolates of gram-negative bacteria. In various animal models of gram-negative bacteremia and endotoxemia, the administration of HA-1A after challenge prevents the development of the dermal Shwartzman reaction and death. (Teng et al. Proc. Natl. Acad. Sci. U.S.A. 82:1790-4, 1985; Ziegler et al. A. Clin. Res. 35:619A, 1987).

HA-1A is produced by continuous-perfusion cell culture and is purified from the supernatant fluid by a series of steps involving selective precipitation and column chromatography. (Ziegler et al. N. Engl. J. Med. 324:429-436, 1991). The cell line that produces HA-1A has been tested extensively and has been shown to be free of human viruses. Furthermore, the purification process for HA-1A includes specific viral-inactivation procedures, and tests are performed to confirm the absence of viruses. None of the lots contained detectable endotoxin in an assay with a sensitivity of 3 pg per milliliter.

Two monoclonal antibodies to endotoxin, E5 and HA-1A, await approval from the Food and Drug Administration. E5, which was developed from murine splenocytes immunized with J5 mutant *E. coli* cells, is an IgM antibody with reactivity to lipid A. (Greenman et al., JAMA 266:1097-1102, 1991). HA-1A is a human IgM antibody (also derived from immunization with J5 mutant cells) that binds specifically to lipid A (Ziegler et al., N. Engl. J. Med. 324:429-436, 1991). Both E5 and HA-1A have been shown to bind to endotoxin from a wide variety of gram-negative bacteria, and both have been evaluated in randomized, double blind, controlled trials.

In an HA-1A study, a single 100-mg intravenous dose of antibody was administered to 262 patients; 281 received placebo. (Ziegler et al. N. Engl. J. Med. 324:429-436, 1991). Active treatment produced a 39% decrease in 28-day mortality among the 200 patients with gram-negative bacteremia (37% of all study patients). Treatment benefit extended to the 101 patients with gram-negative bacteremia who were in shock (defined as a systolic blood pressure of <90 mm Hg or the use of vasopressors to maintain blood pressure) at study entry; in this subgroup, active treatment reduced 28-day mortality by 42%. Among patients with gram-negative bacteremia, active treatment increased the organ failure resolution. All evidence of organ failure disappeared within 7 days in 38 of 61 patients (62%) given HA-1A and in 26 of 62 patients (42%) given placebo.

Some investigators have reported negative results with anti-endotoxin core antiserum. Most of their studies were performed in mice. Although the reasons for discrepant results are not fully understood, several factors may contribute. (McCabe et al. J. Infect. Dis. 158:291-300, 1988; Ziegler, E. J. J. Infect. Dis. 158:286-290, 1988). These include the relative resistance of rodents to endotoxin, the need to compromise host defenses severely in order to establish satisfactory animal models of gram-negative infection and endotoxemia, and the rather low affinity of cross-reactive anti-endotoxin core antibodies as compared with type-specific antibodies. Recently, Baumgartner et al. (J. Exp. Med. 171:889-96, 1990) reported a lack of protection by a human monoclonal antibody derived from cells isolated from the same original clone as HA-1A, but the antibody was not produced or purified by the laboratory that produced HA-1A. When species resembling humans in endotoxin sensitivity are studied, protection from J5 antibody can be demonstrated (Spier et al. Circ. Shock 28:235-48, 1989). The negative results of Calandra et al. with J5 immunoglobulin in patients with gram-negative septic shock (Calandra et al. J. Infect. Dis. 158:312-9, 1988) may have been due to the absence of IgM in their preparation.

HA-1A has been administered in phase I trials to 15 patients with cancer (Khazaeli et al. J. Biol. Response Mod. 9:178-84, 1990) and in unblinded fashion to 34 patients with sepsis, (Fisher et al. Crit. Care Med. 18:1311-5, 1990) as well as to the 291 patients who received it in the aforedescribed trial. In all these patients, HA-1A was safe, well tolerated, and nonimmunogenic.

Nitric oxide synthase inhibitors administered concomitantly with the anti-endotoxin antibody may include an arginine analog having inhibitory activity toward nitric oxide synthase as described in previous examples. It is expected that lower doses of the anti-endotoxin antibody will be therapeutically effective when administered concomitantly or subsequent to an arginine-free parenteral formulation.

EXAMPLE 4

PREPARATION OF ANTI-TUMOR NECROSIS FACTOR ANTIBODIES

The present example is provided to demonstrate a proposed method for preparing anti-tumor necrosis factor antibodies for use in the herein described therapeutic regimens and methods. Either a polyclonal antibody or monoclonal antibody specific for tumor necrosis factor may be prepared according to methods known to those of skill in the art. For preparation of a polyclonal antibody, immunization techniques wherein an animal is immunized with tumor necrosis factor, may be utilized. Alternatively, monoclonal antibodies may be prepared according to standard hybridoma protocols, wherein the spleen of a tumor necrosis factor-immunized animal is fused to an immortal tumor cell line to provide a hybridoma which produces anti-tumor necrosis factor monoclonal antibodies.

The administration of antibodies to TNFα protects against the lethal effects of subsequent endotoxin challenge in animals (Beutler et al. Science 229:869–871, 1985; Tracey et al. Nature 330:662–664, 1987; Opal et al. J. Infect Dis. 161:1148–1152, 1990; Silva et al. J. Infect. Dis. 162:421–427, 1990); this protection holds even if anti-TNFα antibodies are administered 30 minutes after endotoxin challenge (Hinshaw et al. Circ. Shock. 30:279–292, 1990; Bahrami et al. In: Program and Abstracts of the Second International Congress on the Immune Consequences of Trauma, Shock, and Sepsis: Mechanisms and Therapeutic Approaches; Mar. 6–9, 1991; Munich, Germany, Abstract). Thus, TNFα is believed to play a central role in the development of sepsis, and administration of anti-TNFα antibodies appears to be an attractive method for improving outcome, particularly when used in conjunction with an arginine-free parenteral formulation.

The efficacy of anti-TNF antibodies for treating hypotension in humans was demonstrated in humans by Exley et al. (1990). The anti-TNF antibodies described in Exley et al. (1990) therefore constitute a most particularly preferred monoclonal antibody for use in the present invention. This reference is specifically incorporated herein by reference for this purpose. In a phase 1 study, Exley et al. (Lancet 335:1275–1277, 1990) administered murine IgG monoclonal antibodies to recombinant human TNFα (CB0006) to 14 patients with severe septic shock. Mean arterial pressure increased markedly after CB0006 antibody infusion, and there were no adverse reactions to treatment. A controlled clinical trial of anti-TNFα antibodies is now under way.

A major potential benefit of monoclonal antibodies to TNFα is that such treatment may improve outcome in both gram-negative and gram-positive sepsis. Several factors may limit the success of this agent, however. First, TNFα levels have been detected in only about one third of patients with septic shock (Marks et al. Am. Rev. Respir. Dis. 141:94–97, 1990), possibly because of the short half-life of TNFα in humans (14 to 18 minutes). Thus, anti-TNFα antibodies may be administered too late (or too early) for them to have any effect. Second, several studies have demonstrated that elevated TNFα levels alone are insufficient to produce shock (Silva et al. J. Infect. Dis. 162:454–459., 1990; Sun et al. Am. J. Pathol. 136:949–956, 1990). Third, anti-TNFα antibodies may not be effective against all causes of sepsis.

However, it is contemplated that anti-TNF antibody, when used in conjunction with an arginine-free parenteral formulation described herein, would provide an effective method and regimen for the treatment of hypotension, particularly that hypotension attendant septic shock.

PROPHETIC EXAMPLE 5

ANTI-ENDOTOXIN ANTIBODIES AND ARGININE-FREE TPN FOR TREATMENT OF HYPOTENSION IN SEPTIC SHOCK

This example provides interleukin 1 receptor antagonist (particularly IL 1ra) in combination with an arginine-free parenteral formulation nitric oxide synthase inhibitors for treatment of hypotension.

An IL-1 specific inhibitor has been produced from human monocytes (Seckinger et al. J. Immunol. 139:1541–1545, 1987; Arend et al. J. Immunol. 134:3868–3875, 1985); this inhibitor blocks the binding of IL-1 to its cell surface receptors (Seckinger et al. J. Immunol. 139:1541–1545, 1987). The inhibitor has been cloned, and sequence analysis reveals 40% conserved amino acid homology with IL 1β. It has been renamed the IL-1 receptor antagonist (IL 1ra)(Hannum et al. Nature 343:336–340, 1990; Eisenberg et al. Nature 343:341–346, 1990; Carter et al. Nature 344:633–638, 1990), and it competes with IL-1 for occupancy of surface receptors without agonist effects.

Wakabayashi et al. (FASEB Journal 5:338–343, 1991) have blocked endogenous IL-1 activity by pretreatment with human recombinant IL 1ra in a model of *E. coli*-induced shock in rabbits. The IL ira-treated group received IL 1ra intravenous injection as a 10-ml bolus (10 mg/kg) at t= −15 min, followed by a constant rate (15 $\mu g \cdot kg^{-1} \cdot min^{-1}$) for 4 h. In saline-treated controls, hypotension was sustained for 4 h and death occurred for two of five rabbits; in rabbits treated with the IL 1ra, however, blood pressure was only transiently decreased, returned to pre-*E. coli* levels, and no deaths occurred. The associated leukopenia was also reduced by treatment with the antagonist (P <0.05). Histological examination of lung tissues showed reduced infiltrating neutrophils in the IL 1ra treatment group. Despite the attenuated responses in animals treated with the IL 1ra, circulating TNF and IL 1 levels were nearly identical in both groups. The specific blockade of IL 1 at the receptor level demonstrates an essential role for this cytokine in the pathogenesis of septic shock.

An aspect of the present invention is the concomitant administration of the IL 1ra in combination with an arginine-free parenteral formulation in the treatment of hypotension. The Wakabayashi et al. (1990) article is specifically incorporated herein by reference for the purpose of describing a method for preparing an IL-1 receptor antagonist which may be used in the practice of the present invention.

PROPHETIC EXAMPLE 6

ANTI-ENDOTOXIN ANTIBODIES AND ARGININE-FREE TPN FOR TREATMENT OF HYPOTENSION IN SEPTIC SHOCK

The present example is provided to demonstrate the proposed use of a therapeutic regimen of an arginine-free parenteral formulation and anti-endotoxin antibodies in the treatment of hypotension. More specifically, it is proposed that the present methods and compositions may be used in the treatment of hypotension in patients exposed to endotoxin and/or who have developed septic shock.

The earliest possible intervention in endotoxin (septic) shock involves the use of antibodies directed against endotoxin itself or against cytokines participating in the cascade initiated by endotoxin (i.e., tumor necrosis factor and IL-1) Although antibodies are of no use in studies such as those of Ochoa et al., (1992) *J. Natl. Cancer Inst.*, 84:854–867, where a cytokine is used therapeutically, antibodies show some clinical activity in septic shock (Ziegler et al. (1991) *N. Eng. J. Med.* 324:429–437); Baumgartner et al. (1990) *J. Exp. Med.* 171:889–896; Calandra et al. (1988) *J. Infect. Dis.* 158:312–319. The advantages of antibody therapy are that all adverse effects of endotoxin can, in principle, be avoided and that constitutive nitric oxide synthase is not inhibited. Antibodies should most preferably be given before nitric oxide synthase is induced. Once induced, nitric oxide synthase may remain active for 24–48 hours. In a clinical setting, NO mediated shock cannot be anticipated with the necessary degree of certainty.

Antibodies directed against endotoxins will be prepared as described herein using immunization protocols of an animal injected with endotoxin, or by standard hybridoma technology well known to those of skill in the art. Example 3 outlines one potential method for the preparation of these antibodies. The most preferred anti-endotoxin antibody for use in the invention is HA-1A, previously described. A commercial source of endotoxin is available from suppliers such as Sigma Chemical Co. (St. Louis, Mo.).

The anti-endotoxin antibody would preferably be administered to the patient concurrently with the administration of an arginine-free TPN. The arginine-free TPN is described in Example 1, and most preferably will include citrulline, ornithine, or both, to even further satisfy urea cycle requirements in the animal.

A therapeutically effective concentration of the anti-endotoxin antibody will be determined on the basis of patient response as an improvement of the hypotensive condition. An improvement in the hypotensive condition as defined for purposes of describing the present invention, is demonstrated by an increase in systolic pressure to at least 100 mm Hg in the patient. A systolic blood pressure of at least 100 mm Hg is defined for purposes of describing the present invention as a normotensive condition. The antibodies are most preferably to be administered before nitric oxide synthase induction to be fully effective.

PROPHETIC EXAMPLE 7

INTERLEUKIN-1 RECEPTOR ANTAGONISTS AND ARGININE-FREE TPN FOR TREATMENT OF HYPOTENSION

The present example is provided to outline a proposed method for the treatment of hypotension in an animal, particularly that hypotension attendant exposure to endotoxin or septic shock, through the use of an arginine-free parenteral formulation and an interleukin-1 receptor antagonist. The most preferred interleukin-1 receptor antagonists for use in conjunction with the present invention may be obtained from, or prepared according to the method outlined in Wakabayashi et al. (1991)[10], which reference is specifically incorporated herein by reference for this purpose.

By way of example, the specific interleukin-1 receptor antagonist to be used is IL ira. This interleukin-1 receptor antagonist is described in Wakabayashi et al. (1991)[10], and is most preferably to be administered via a bolus intravenous infusion of between about 1 mg/kg to about 100 mg/kg, with the most preferred dose being about 10 mg/kg.

The arginine-free parenteral formulation is to be prepared as described in Example 1. A patient having a systolic blood pressure of less than about 100 mm Hg will be targeted for the present treatment. Such a patient is to be placed on a continuous feed of an arginine-free formulation which includes a mixture of essential and nonessential amino acids as described in Example 1. The formulation, in one embodiment, may be supplemented with between 1–2 g/l ornithine and/or between 1–2 g/l citrulline. The patient is to be maintained on the arginine-free TPN concurrently with the interleukin-1 antagonist. Blood samples are to be obtained from the patient and arginine levels in the serum or plasma fraction are to be determined. The patient is to be given an intravenous bolus dose of interleukin-1 receptor antagonist, most preferably IL-1 ra. This particular interleukin-1 receptor antagonist is described in Wakabayashi et al. (1991)[10], which reference is specifically incorporated herein by reference for this purpose.

Tachycardia (>90 beats per minute in the absence of beta-blockade) and tachypnea (respiratory rate >20 beats per minute or the requirement of mechanical ventilation) have been characterized as signs of systemic toxicity (Ziegler et al. (1991) *The New England Journal of Medicine*, 324(7):429–436). With the combination therapeutic regimen described herein, the treated patient may also be free of these systemic toxicity symptoms as well as exhibiting normotensive systolic blood pressure.

The blood pressure of the patient may be monitored, for example using a cuff-blood pressure monitoring device, after the interleukin-1 receptor antagonist is administered. The patient is to be maintained on the continuous parenteral feed of the arginine-free TPN both before and after the antagonist is administered. A return to normotensive blood pressure levels (at least 100 mm Hg systolic blood pressure) may result in the patient upon treatment according to the claimed method. Reduction in serum/plasma arginine levels in combination with the antagonist may provide relief from other signs of systemic toxicity, unlike previous reports using the antagonist alone (IL 1ra).

PROPHETIC EXAMPLE 8

ANTI-TUMOR NECROSIS FACTOR AND ARGININE-FREE TPN FOR TREATMENT OF HYPOTENSION

The present example is provided to demonstrate one preferred method by which the herein described therapeutic regimen and methods may be employed for the treatment of hypotension.

Anti-tumor necrosis factor antibodies may be prepared as described by Calandra et al. (1991), In: Bacterial Endotoxins: Cytokines Mediators and New Therapies for Sepsis, pp. 141-159), which reference is specifically incorporated herein by reference for this purpose. By way of example, such anti-tumor necrosis factor antibodies include a polyclonal anti-TNF antibody described by Beutler et al., which reference is specifically incorporated herein by reference for this purpose (Beutler et al. (1985), Science, 229:869–871). An anti-TNF monoclonal antibody may be used for the herein described methods as well, and is a more particularly preferred aspect of the claimed invention. Such a monoclonal antibody for TNF is described by Tracey et al. (1987), Nature, 330:662–664. The Tracey et al. article is also incorporated herein by reference for the purpose of describing a method for preparing the anti-TNF monoclonal antibodies which may be used in conjunction with the herein claimed combination therapeutic regimens and methods. Such an anti-TNF monoclonal antibody preferred is CB0006 (see Example 4).

A patient is first to be identified as having hypotension, a condition which is described for purposes of the present invention as a systolic blood pressure of less than about 100 mm Hg. Once a patient has been determined to have a hypotensive condition, he or she is to be started on an parenteral formulation which is arginine-free. The arginine-free TPN is defined compositionally herein at Example 1. This formulation may also include citrulline and/or ornithine so as to insure metabolic requirements of the urea cycle in the animal. The animal or patient is to be maintained on the arginine-free TPN until serum or plasma arginine levels have been reduced. For this reason, the patient or animal is to be monitored continuously for changes in arginine concentrations in serum and/or plasma samples.

A bolus dose of the anti-TNF antibody, most preferably a monoclonal anti-TNF antibody as described in Exley et al. (1989) (Murine monoclonal antibody to recombinant human tumor necrosis factor in the treatment of patients with severe septic shock. Abstract No. 324. Program and abstracts of the 29th interscience conference on anti-microbial agents and chemotherapy, 155) is administered to the patient simultaneously with the arginine-free parenteral formulation. Thus, during administration of the anti-TNF antibody, the patient and/or animal is to be maintained on the arginine-free parenteral formulation. Upon such treatment, the patient and/or animal may demonstrate an increase in systemic blood pressure levels to normotensive levels (i.e., at least about 100 nun Hg).

Treatment of patients with severe systemic shock with a murine monoclonal antibody to recombinant human TNF (anti-rhTNF) was reported in the Exley et al. (1989) study, with a reversal of hypotension in nine of ten patients. However, 50% of these patients reported died within 7 days of attaining normotensive levels. Such a mortality rate is reported by those authors as relatively the same as mortality rates in patients with septic shock receiving no treatment (see Calandra et al. (1988). Therefore, no protection against death is observed when anti-TNF antibodies are used alone after an infectious challenge. Administration of an arginine-free total parenteral formulation to the patient prior to and concurrently with the antibody treatment may provide for an enhancement in patient survival and improvement in patient mortality.

EXAMPLE 9

The present example demonstrates the effects of interleukin-1 receptor antagonists on the induction of nitric oxide synthase by IL-1 or IL-1 plus IFN-α. While the results demonstrate in vitro results, the data is also indicative of those effects to be expected from the use of interleukin-1 receptor antagonist in vivo.

This example demonstrates inhibition of IL-1-α-induced nitric oxide synthase in vascular smooth muscle.

MATERIALS AND METHODS

Materials

Human recombinant, IL-1-α (hereinafter referred to as IL-1; specific activity, $2 \times 10^9$ lymphocyte-activating factor units/mg) was produced by Dainippon Pharmaceutical Co., Ltd. (Osaka, Japan) and provided by the National Cancer Institute. Human recombinant Il-1 receptor antagonist was produced by Synergen (Boulder, Colo.). Rat interferon-γ (IFN-γ) was obtained from Amgen Biologicals (Thousand Oaks. Calif.) Except where indicated, all biochemical reagents were obtained from Sigma Chemical Co. (St. Louis, Mo.). Cell culture media and reagents, unless otherwise noted, were from Whittaker Bioproducts (Walkersville, Md.).

Cell Culture

Mouse A375 melanoma cells were provided by Dr. E. Kleinerman, The University of Texas M.D. Anderson Cancer Center. Cells were maintained in Dulbecco's modified Eagle medium and Ham's F-12 medium (1:1) containing 10 mM HEPES buffer (pH 7.4) and 10% fetal bovine serum. All tissue culture reagents contained less than 0.25 ng/mL endotoxin as measured by the limulus amebocyte assay. Murine D10 T cells were obtained from the American Type Culture Collection (Rockville, Md.).

Aortic smooth muscle cells were cultured by explanting segments of the medial layer of aortas from adult male Fischer 344 rats. Aortas were removed aseptically and freed of adventitial and endothelial cells by scraping both the luminal and abluminal surfaces. Medial fragments were allowed to attach to Primaria 25-cm² tissue culture flasks (Becton-Dickinson, Lincoln Park, N.J.) which were kept moist with growth medium until cells emerged. Cultures were fed twice weekly with medium 199 containing 10% fetal bovine serum, 25 mM HEPES buffer (pH 7.4), 2mM L-glutamine, 40 μg/mL endothelial cell growth supplement (Biomedical Technologies, Inc., Stoughton, Mass.) and 10 μg/ml gentamicin (GIBCO BRL, Grand Island, N.Y.). When primary cultures became confluent, they were passaged by trypsinization, and explants were discarded. For these studies, cells from passages 12–14 were seeded at 20,000 per well in 96-well plates and were used at confluence (60,000–80,000 cells per well). The cell exhibited the classic smooth muscle cell phenotype with hill and valley morphology, and they stained positively for smooth muscle actin.

Cell Respiration Assay

Rat aortic smooth muscle cells in 96-well microtiter plates were incubated for 90 minutes in RPMI-1640 medium containing 0.2 mg/mL 3-(4,5 dimethylthiazol-2-γl)-2,5-diphenyltetrazolium bromide (MTT), washed with Hanks' balanced salt solution, and solubilized in 100 μL of dimethyl sulfoxide. The extent of reduction of MTT to formazan within cells, quantitated by measurement of the optical density at 550 nm ($OD_{550}$), was taken as an indicator of cellular respiration (Klostergaard, J., et al. J. Immunol. Methods 101:97–108, 1987).

IL-1-Induced Cell Proliferation Assay

Murine D10 cells, an IL-1 dependent T-cell line, were used to measure IL-1 mitogenic activity. Cell proliferation in the present of IL-1 was assessed by incorporation of ($^3$H) thymidine as previously described (Bakouche, O., et al. J. Immunol. 138:4249–4255, 1987).

IL-1-Induced Cytotoxicity Assay

IL-1-induced cytotoxicity was studied using A375 tumor cells plated at a density of 6000 cells per well in 96-well microliter plates. After overnight attachment, IL-1 (3–300 ng/mL) was added in the presence or absence of NAA or NMA. After cells were incubated for 3 days, ($^3$H) thymidine was added (1 $\mu$Ci per well) for an additional 2 hours. Cells were harvested onto glass fiber disks (PHD Cell Harvested; Cambridge Technology, Inc., Watertown, Ma.) Disks were air dried overnight, and radioactivity was determined with a Model 1900TR Scintillation Counter (Packard Instrument Division, Downers Grove, Ill.)

Induction and Assay of Nitrite Synthesis in Smooth Muscle Cells

Rat aortic smooth muscle cells were incubated with RPMI-1640 medium containing 10% bovine calf serum, 25 mM HEPES buffer 7.4), 2 mM glutamine, 80 U/mL penicillin, 80 $\mu$g/mL streptomycin, 2 $\mu$g/mL fungizone, and IL-1, IFN-$\gamma$, and various inhibitors at the concentrations indicated in the figure legends. At the desired times, nitrite concentration in the culture medium was measured using the standard Griess assay (Green, L., et al. Anal. Biochem. 126:131–138, 1982) adapted to a 96-well microtiter plate reader (Gross, S. S., et al. Biochem. Biophys. Res. Commun. 178:823–829, 1991). Thus, 100 $\mu$L of Griess reagent (0.5% sulfanilic acid, 0.05% naphthalenediamine, and 2.5% phosphoric acid) was added to an equal volume of culture medium, and the OD$_{550}$ was measured and related to nitrite concentration by reference to a standard curve. The background OD$_{550}$ of medium incubated in the absence of cells was subtracted from experimental values.

Preparation and Assay of Smooth Muscle Cell NO Synthase

Rat aortic smooth muscle cells were incubated with RPMI-1640 medium containing 10% bovine calf serum, 25 mM HEPES buffer (pH 7.4), 2 mM glutamine, 80 $\mu$g/mL penicillin, 80 $\mu$g/mL steptomycin, 2 $\mu$g/mL fungizone, 30 $\mu$g/mL lipopolysaccharide (*Escherichia coli* 0111:B4), and 50 U/mL IFN-y. Cells were harvested after 24 hours, and cytosol was prepared (Gross, S. S., et al. Biochem. Biophys. Res. Commun. 178:823–829, 1991). Cytosolic NO synthase activity was assayed by the Fe$^{2+}$-myoglobin method described previously (Gross, S. S., et al. Biochem. Biophys. Res. Commun. 178:823–829, 1991).

RESULTS

Induction of Nitric Oxide Synthase in Vascular Smooth Muscle Cells

When grown in the absence of biological response modifiers, rat aortic smooth muscle cells showed no evidence of nitric oxide synthase activity. When cultured in the presence of human recombinant IL-1 (40 ng/mL), however, these cells formed and released substantial amounts of nitrite, a stable degradation product of NO. Nitrite synthesis was evident within 14 hours and continued to increase for at least 40 hours (FIG. 28). These observations are in accord with recent reports that IL-1 induces rat (Beasley, D., et al. J. Clin. Invest 87:602–608, 1991) and rabbit (Busse & Mulsch Febs Lett. 275:87–90, 1990) aortic smooth muscle cells in culture to release a factor that activates guanylate cyclase and decays to nitrite. As shown in FIG. 28, IFN-$\gamma$, which does not itself induce nitric oxide synthase in smooth muscle cells, significantly enhanced the induction of synthase by IL-1. IL-1 receptor antagonist inhibited the induction of nitric oxide synthase by IL-1 or IL-1 plus IFN-$\gamma$ by more than 98%. Concentration levels of IL-1 as low as 1 ng/mL induced detectable nitric oxide synthase activity in smooth muscle cells; the ED$_{50}$ (i.e., dose which gives a response that is 50% of maximum) values for IL-1 alone and for IL-1 plus IFN-$\gamma$ were about 5 ng/mL and 1 ng/mL, respectively (FIG. 28, Panel B).

Induction of nitric oxide synthase was dependent on both RNA and protein synthesis. Thus, control monolayers of smooth muscle cells cultured for 14 hours in the presence of IL-1 (100 ng/mL) and IFN-$\gamma$ (50 ng/mL) produced 2.52=0.28 mnol (mean ±SD) of nitrite when transferred to cytokine-free medium and cultured for an additional 16 hours. Equal numbers of smooth muscle cells cultured similarly in medium supplemented with either 0.5 mg/mL of dactinomycin or 1 mg/mL of cycloheximide produced less than 0.1 nmol of nitrite. Neither dactinomycin nor cycloheximide adversely affected cell viability under these conditions, as judged by reduction of MTT, a measure of mitochondrial respiration. (MTT reduction [mean ±SD] by dactinomycin- and cycloheximide-treated IL-1-activated cells was 101%±6% and 95%±7%, respectively, of that measured in control cells that were treated with IL-1 alone.)

BIBLIOGRAPHY

The following references, insomuch as they supplement details and even further define particular aspects of protocols presented in the present disclosure, are specifically incorporated herein by reference for such purposes as may be indicated herein.

1. Kilbourn R. G., Jubran A., Griffith O. W., Gross S. S., Levi R., Adams J., and Lodato R. F. (1990), Reversal of endotoxin-mediated shock by N$^G$-methyl-L-arginine, an inhibitor of nitric oxide synthesis. *Biochem. Biophys. Res. Commun.*, 172(3):1132–1138.

2. Sakuman I., Stuehr D., Gross S., Nathan C., and Levi R. (Nov. 1988), Identification of arginine as a precursor of endothelium derived relaxing factor (nitric oxide). *Natl. Academy Sci.*, 85:8664–8667.

3. Palmer R., Rees D., Ashton D. and Moncada S. (June 1988), L-Arginine is the physiological precursor for the formation of nitric oxide in endothelium relaxation. *Biochem. Biophys. Res. Commun.*, 153:1251–1256.

4. Hibbs J., Vavrin Z., Tiator R. R. (Jan. 15, 1987), L-arginine is required for the expression of the activated macrophage effector mechanism causing selective metabolic inhibition in target cells. *J. Immunol.*, 138:550–565.

5. Ziegler E. J. et al. (1991), Treatment of Gram-Negative Bacteremia and Septic Shock with HA-1A Human Monoclonal Antibody Against Endotoxin. *The New England Journal of Medicine*, 324(7):429–436.

6. Baumgartner J. D. et al. (1990), Association Between Protective Efficacy of Anti-Lipopolysaccharide (LPS) Antibodies and Suppression of LPS-Induced Tumor Necrosis Factor α and Interleukin 6. *J. Exp. Med.*, 171:889-896.

7. Calandra T. et al. (1988), Treatment of Gram-Negative Septic Shock with Human IgG Antibody to *Escherichia coli* J5: A Prospective, Double-Blind, Randomized Trial. *The Journal of Infectious Diseases*, 158(2):312-319.

8. Roger C. Bone (1991), A Critical Evaluation of New Agents for the Treatment of Sepsis. *JAMA*, 266(12):1686-1691.

9. Opal S. M. et al. (1991), Efficacy of Anti-lipopolysaccharide and Anti-Tumor Necrosis Factor Monoclonal Antibodies in a Neutropenic Rat Model of *Pseudomonas Sepsis*. *J. Clin. Invest.*, 88:885-890.

10. Wakabayashi G. O. et al. (1991), A Specific receptor antagonist for interleukin 1 prevents *Escherichia coli*-induced shock in rabbits. *FASEB*, 5:338-343.

11. Wolfe S. M. (1991), Monoclonal Antibodies and the Treatment of Gram-Negative Bacteremia and Shock. *The New England Journal of Medicine*, 324(7):486-488.

12. Calandra T. et al. (1991), Anti-Lipopolysaccharide and Anti-tumor Necrosis Factor/Cachectin Antibodies for the Treatment of Gram-Negative Bacteremia and Septic Shock, In *Bacterial Endotoxins: Cytokine Mediators and New Therapies for Sepsis*, pp. 141-159.

13. Eisenberg S. P. et al. (1990), Primary structure and functional expression from complementary DNA of a human interleukin-1 receptor antagonist. *Nature*, 343:341-346

14. Hannum C. H. et al. (1990), Interleukin-1 receptor antagonist activity of a human interleukin-1 inhibitor. *Nature*, 343:336-340.

15. Carter D. B. et al. (1990), Purification, cloning, expression and biological characterization of an interleukin-1 receptor antagonist protein. *Nature*, 344:633-638.

16. Teng, N. N. H. et al. (1985), Protection against Gram-negative bacteremia and endotoxemia with human monoclonal IgM antibodies. *Proc. Natl. Acad. Sci USA*, 82:1790-1794.

17. Ajani et al. U.S. Pat. No. 4,988,724 dated Jan. 29, 1991.

18. Ajani et al. U.S. Pat. No. 4,859,452 dated Aug. 22, 1989.

What is claimed is:

1. A therapeutic regimen comprising a therapeutically effective amount of an arginine-free formulation of amino acids and a therapeutically effective amount of an interleukin-1 receptor antagonist, wherein said formulation comprises a mixture of essential and non-essential amino acids together in a pharmacologically acceptable excipient.

2. The therapeutic regimen of claim 1, wherein the formulation includes:
about 3-4 g/l isoleucine;
about 4-6 g/l leucine;
about 3-4 g/l lysine;
about 1-2 g/l methionine;
about 1-2 g/l phenylalanine;
about 2-3 g/l threonine;
about 0.5-1.5 g/l tryptophan;
about 3-4 g/l valine;
about 4-5 g/l alanine;
about 1-2 g/l histidine;
about 3-4 g/l proline;
about 1-2 g/l serine;
about 0.25-0.75 g/l tyrosine;
about 4-5 g/l glycine; and
about 2-3 g/l aspattic acid,
together in a pharmacologically acceptable excipient.

3. The therapeutic regimen of claim 2, wherein the formulation further includes ornithine at a concentration of about 1-2 g/l.

4. The therapeutic regimen of claim 2, wherein the formulation includes citrulline at a concentration of about 1-2 g/l.

5. The therapeutic regimen of claim 2, wherein the interleukin-1 receptor antagonist is administered intravenously.

6. The therapeutic regimen of claim 2 wherein the interleukin-1 receptor antagonist is IL 1ra.

7. The therapeutic regimen of claim 2 wherein the arginine-free formulation is a parenteral formulation.

8. The therapeutic regimen of claim 2 wherein the formulation is administered concurrently with the interleukin-1 receptor antagonist.

9. The therapeutic regimen of claim 1 or 5 wherein the regimen is anti-hypotensive.

10. A method for treating chemotherapeutic agent-related hypotension comprising:
monitoring an animal receiving a chemotherapeutic agent for a decrease in systolic blood pressure to less than about 100 mm Hg to detect an animal with systemic hypotension;
treating the animal having systemic hypotension with a therapeutic regimen comprising a therapeutically effective amount of arginine-free formulation of amino acids sufficient to reduce plasma or serum arginine concentration administered concurrently with or followed by the administration of a therapeutically effective concentration of an interleukin-1 receptor antagonist or an anti-tumor necrosis factor antibody; and
maintaining the animal on the therapeutic regimen until an increase of systolic blood pressure to at least about 100 mm Hg is detectable.

11. The method of claim 10, wherein the animal is a human.

12. The method of claim 10 wherein the arginine-free formulation is a parenteral formulation.

13. The method of claim 10 wherein the interleukin-1 receptor antagonist is IL 1ra.

14. The method of claim 10 wherein the therapeutic regimen includes an interleukin-1 receptor antagonist and the chemotherapeutic agent is tumor necrosis factor or interleukin-2.

15. The method of claim 10, wherein the arginine-free parenteral formulation includes:
about 3-4 g/l isoleucine;
about 4-6 g/l leucine;
about 3-4 g/l lysine;
about 1-2 g/l methionine;
about 1-2 g/l phenylalanine;
about 2-3 g/l threonine;
about 0.5-1.5 g/l tryptophan;
about 3-4 g/l valine;
about 4-5 g/l alanine;
about 1-2 g/l histidine;
about 3-4 g/l proline;
about 1-2 g/l serine;
about 0.25-0.75 g/l tyrosine;
about 4-5 g/l glycine; and about 2–3 g/l aspartic acid, together in a pharmacologically acceptable excipient.

16. The method of claim 15, wherein the parenteral formulation comprises ornithine at a concentration of about 1–2 g/l.

17. The method of claim 15, wherein the parenteral formulation comprises citrulline at a concentration of about 1–2 g/l.

18. The method of claim 10, wherein the therapeutically effective concentration of the interleukin-1 receptor antagonist is between about 1 mg/kg to about 100 mg/kg.

19. The method of claim 10, wherein the therapeutically effective concentration of the interleukin-1 receptor antagonist is about 10 mg/kg.

20. The method of claim 10 wherein the arginine-free formulation is administered concurrently with the interleukin-1 receptor antagonist or anti-tumor necrosis factor antibody.

21. A method for treating septic shock-related hypotension in an animal exposed to endotoxin comprising:

treating the animal with a therapeutically effective amount of an arginine-free formulation of amino acids sufficient to reduce plasma or serum arginine levels in the animal concurrently with an interleukin-1 receptor antagonist or an anti-endotoxin antibody;

monitoring the blood pressure of the animal, and maintaining the animal on the arginine-free formulation until a systolic blood pressure of at least 100 mm Hg is detected.

22. The method of claim 21 wherein the interleukin-1 receptor antagonist is IL 1ra and the anti-endotoxin antibody is HA-1A.

23. The method of claim 21 wherein the arginine-free formulation is a parenteral formulation.

* * * * *